(12) United States Patent
Shapiro et al.

(10) Patent No.: US 8,185,191 B1
(45) Date of Patent: May 22, 2012

(54) PULSE MONITORING AND WARNING SYSTEM FOR INFANTS

(75) Inventors: Michael Evan Shapiro, Reno, NV (US); Joe Paul Tupin, Rocklin, CA (US)

(73) Assignees: Michael Evan Shapiro, Reno, NV (US); Baby Technologies, LP, Reno, NV (US)

( * ) Notice: Subject to any disclaimer, the term of this patent is extended or adjusted under 35 U.S.C. 154(b) by 1347 days.

(21) Appl. No.: 11/672,828

(22) Filed: Feb. 8, 2007

Related U.S. Application Data

(63) Continuation-in-part of application No. 11/026,334, filed on Dec. 29, 2004, now abandoned.

(60) Provisional application No. 60/533,705, filed on Dec. 29, 2003.

(51) Int. Cl.
*A61B 5/02* (2006.01)
(52) U.S. Cl. ......... 600/521; 600/500; 600/508; 600/509
(58) Field of Classification Search .................. 600/500, 600/503, 502, 521
See application file for complete search history.

(56) References Cited

U.S. PATENT DOCUMENTS

| | | | | |
|---|---|---|---|---|
| 4,546,776 A | * | 10/1985 | Bellin et al. | 600/517 |
| 5,697,378 A | * | 12/1997 | Elghazzawi | 600/508 |
| 5,941,837 A | * | 8/1999 | Amano et al. | 600/595 |
| 6,361,502 B1 | * | 3/2002 | Puolakanaho et al. | 600/508 |

\* cited by examiner

*Primary Examiner* — Patricia Mallari

(57) ABSTRACT

A pulse monitoring and warning method and system comprising a sensor disposable over an individual's heart and configured to sense a heart rate, the sensor configured to transmit a wireless signal; and a monitor configured to continuously receive a wireless signal from the sensor, the monitor configured to process the signal and produce an alert indication responsive to the heart rate falling below a predetermined level. The system and method employ a QRS detection algorithm, which includes several mechanisms for minimizing the impact of amplitude fluctuation, EMG interference and P/T segment interference. These mechanisms include a variable QRS detection threshold algorithm, a variable QRS search window algorithm, a QRS segment slope/width detector algorithm, and a QRS reacquisition procedure.

19 Claims, 7 Drawing Sheets

PULSE MONITORING AND WARNING SYSTEM FOR INFANTS

CROSS-REFERENCE TO RELATED APPLICATIONS

This application is a Continuation-in-Part of co-pending U.S. patent application Ser. No. 11/026,334, filed Dec. 29, 2004, which claims priority to U.S. Provisional Patent Application Ser. No. 60/533,705, filed Dec. 29, 2003, both of which are hereby incorporated by reference as if set forth herein.

BACKGROUND

The present disclosure relates to a pulse monitoring and warning system for infants. Over 1,000 babies die of Sudden Infant Death Syndrome (SIDS) (or crib death) each year in the United States alone. SIDS is the sudden death of an infant under one year of age, which remains unexplained after a thorough case investigation. The infant that dies from SIDS is often placed in a bed and dies during a nap or evening sleeping. At those times of the day, even the most vigilant parent is not fully aware of the physical condition of the infant.

The prior art provides baby monitors that sense the sounds near the baby. The prior art monitors are useful in alerting a parent of sounds that a baby may make while in a crib. The baby can be heard while crying or playing with objects in the crib. The prior art audible indicators are effective for the purpose of monitoring a baby in a limited way. The prior art also employs video monitors that can enhance the audible monitors. The video monitors detect the movements of the baby and can include audible indications as well. The audible monitors are relatively inexpensive to purchase and thus, are very commonly owned and used. The video systems are more costly and not used as frequently.

However, despite the utility of the prior art systems, the prior art systems fall short of preventing SIDS. Even though a parent is listening and even watching a video monitor, a sleeping baby lying down still provides no indication of distress if succumbing to SIDS. The prior art systems do not adequately provide warning of danger to the child. Currently, there is no device that is directed towards measuring a baby's heart rate in order to prevent SIDS and that is designed for practical home use.

What is needed in the art is a device for accurately monitoring the heart rate of an infant having a means for relaying that heart rate to a monitor.

SUMMARY

The disclosed device is directed towards a pulse monitoring and warning system for infants to actively monitor the heart rate of a sleeping infant through the use of a sensor. If the infant's heart rate were to fall below an acceptable rate, above an acceptable rate, or outside an acceptable range, the sensor would wirelessly transmit the decreased heart rate to the monitor and sound an alarm to alert the parents of the sleeping infant.

A pulse monitoring and warning method and system is disclosed, comprising a sensor disposable over an individual's heart and configured to sense a heart rate, the sensor configured to transmit a wireless signal; and a monitor configured to continuously receive a wireless signal from the sensor, the monitor configured to process the signal and produce an alert indication responsive to the heart rate falling below a predetermined level, above a predetermined level, or outside a predetermined range. The system and method employ a QRS detection algorithm, which includes several mechanisms for minimizing the impact of amplitude fluctuation, EMG interference and P/T segment interference. These mechanisms may include a variable QRS detection threshold algorithm, a variable QRS search window algorithm, a QRS segment slope/width detector algorithm, and a QRS reacquisition procedure.

DETAILED DESCRIPTION

Persons of ordinary skill in the art will realize that the following description of the present disclosure is illustrative only and not in any way limiting. Other embodiments of the invention will readily suggest themselves to such skilled persons having the benefit of this disclosure.

The pulse monitoring and warning system for infants actively monitors the heart rate of a sleeping infant. A baby's typical heart rate is between about 80 beats per minute to about 200 beats per minute. A sensor disposed over the heart of a sleeping infant actively transmits the heart rate to a monitor. If the infant's heart rate falls below an acceptable rate, above an acceptable rate, or outside an acceptable range, the monitor will detect the rate and sound an alarm to alert the parents of the sleeping infant. Because of the wireless nature of the system, the parents are able to monitor the sleeping infant's heart rate remotely.

Figure 1:
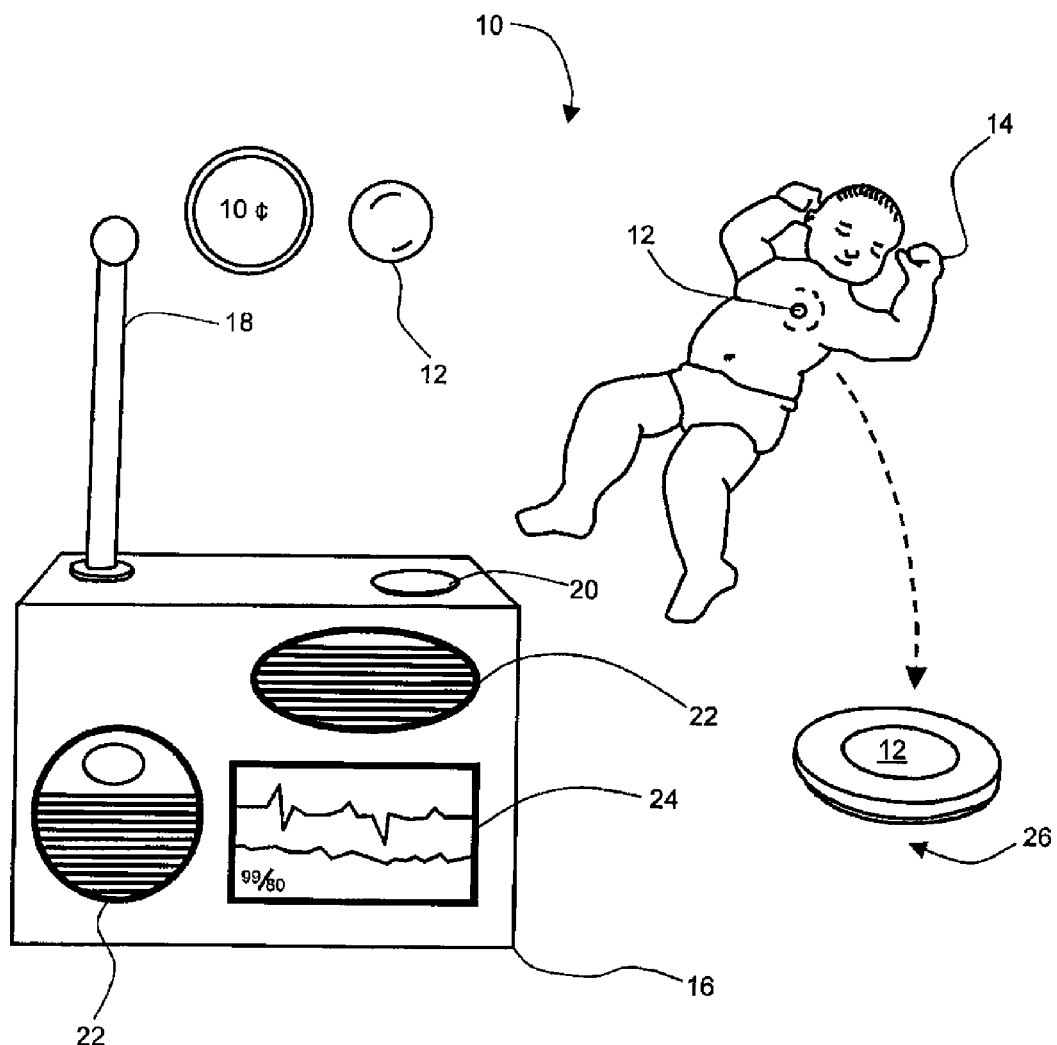
FIG. 1 is a perspective view of an exemplary pulse monitoring and warning system for infants in accordance with the present invention.

Referring to FIG. 1, an exemplary pulse monitoring and warning system 10 for infants is illustrated. The pulse monitoring and warning system 10 includes a sensor 12 that is disposed over the heart of an infant 14. The sensor 12 can wirelessly transmit the infant's heart rate to a receiver (not illustrated) in a monitor 16. The sensor 12 includes a sensing element, a processor, and a transmitter, (not shown) for sensing the heart rate, processing the signal, and transmitting the signal. The sensing element may be any device, or combination of devices, suitable for sensing the heart rate including, but not limited to, a lead or an electrode commonly used in the field of electrocardiography.

One advantage of the present invention is that it can work with only two sensing elements. Although multiple sensing elements may be used, preferably only two are used, thereby reducing the amount of material attached to the skin of the infant and resulting in less irritation and complication. The sensor 12 may also include a battery (not illustrated).

In a preferred embodiment, the sensing elements, such as the electrodes, are disposable and used for a limited period of time. The disposable sensing elements can improve hygiene for the baby. In another embodiment, the sensing elements can be sanitized for reuse. The monitor 16 can be equipped with an antenna 18, an on/off button 20, a speaker 22, and a visual display 24.

The sensor 12 can be formed in a variety of different sizes. For example, the sensor 12 may have a width of about 5 cm and be about 1/16 inch thick. The sensor 12 is attached to the chest of an infant 14 in a place that will produce the maximum impulse for providing precise and reliable monitoring, otherwise known as the Point of Maximum Impulse (PMI). It is recommended that the sensor 12 be slightly moved with each usage to reduce the risk of skin irritation to the infant 14. The sensor 12 can be disposed on the infant 14 using an adhesive 26 that is compatible with the sensitive skin of an infant 14. Preferably, water-soluble gel sensors are utilized. It is recommended that the sensor 12 be worn under clothing at all times to prevent dislodging of the sensor 12 by the infant 14. This will serve to reduce the risk of any choking hazard.

The sensor 12 may continuously transmits wirelessly (i.e., radio wave) the infant's heart rate to a receiver (not illustrated) in a monitor 16. In a preferred embodiment, a burst mode transmitter is used in order to conserve battery power, where data is transmitted after every heartbeat or every 2 seconds, whichever comes first. The monitor 16 is similar to a typical baby monitor with the exception that the monitor 16 continuously monitors the infant's heart rate. The monitor 16 is preferably about 4 inches tall by about 6 inches wide by about 2 inches thick. The monitor 16 can be made of plastic, metal, combinations thereof, and the like. The monitor 16 should be placed within an acceptable distance from the sensor 12 in order to receive a strong signal from the sensor 12.

Since the system 10 is wireless, the infant 14, sensor 12 and monitor 16 can all be moved easily without any concern about tangling or otherwise damaging wires. The sensor 12 (on the infant 14) and the monitor 16 can also be moved separately as individual components, instead of having to be transported simultaneously in order to maintain the wire connection. This wireless configuration allows for greater flexibility in terms of manipulating the sensor 12 and the monitor 16.

The monitor 16 can be equipped with an on/off button 20. The monitor 16 can be battery operated or have a DC connection, or both. The monitor can be equipped with an antenna 18 that receives the wireless signal from the sensor 12 and transmits the signal to the transceiver (not shown). The monitor 16 can be equipped with a processor (not shown) that interprets the signal in order to sound the alarm. The monitor 16 can also be equipped with a speaker 22 for producing an alarm (i.e., a bell, buzz, or other appropriate audible sound) to alert the parents when the heart rate of the infant 14 falls outside the acceptable range. The monitor 16 can also be equipped with a visual display 24 for demonstrating visually the heart rate of the infant.

Although the present invention works with just one monitor, multiple monitors may be used in order to provide a strong enough signal to a monitor that is positioned in a location too remote from the sensor 12 to receive the transmitted signal. Since the monitor 16 may include a transceiver, it also has the ability to transmit the signal sent to it by the sensor 12. Therefore, a first monitor that is placed within an acceptable distance from the sensor 12 for receiving a strong signal from the sensor 12 may relay the signal to a second monitor that is outside the acceptable distance from the sensor 12, but within an acceptable distance from the first monitor. For example, the first monitor may be placed in the infant's room within an acceptable distance from the sensor 12, while the second monitor may be placed in the parents' room, outside of the acceptable distance from the sensor 12, but within an acceptable distance from the first monitor in the infant's room.

The monitor 16 may be combined with audible monitors, allowing a parent to monitor the infant's sounds and heart rate with one system. The monitor 16 may also be combined with video monitors in order to provide a parent with the ability to monitor the infant's movements and heart rate with one system. The monitor 16 can even be combined with both an audible monitor and a video monitor, thereby allowing a parent to monitor the infant's sounds, movements and heart rate all with one system.

The present invention also comprises a useful, novel, and non-obvious method and device for detecting and tracking the human electrocardiogram (ECG) signal. In a preferred embodiment, the steps for detecting and tracking the ECG signal are embodied in machine-executable instructions. These instructions can be used to cause a general-purpose or special-purpose processor that is programmed with the instructions to perform the steps of the present invention. Alternatively, the steps of the present invention might be performed by specific hardware components that contain hardwired logic for performing the steps, or by any combination of programmed computer components and custom hardware components.

The present invention may be provided as a computer program product that may include a machine-readable medium having stored thereon instructions that may be used to program a computer (or other electronic devices) to perform a process according to the present invention. The machine-readable medium may include, but is not limited to, floppy diskettes, optical disks, CD-ROMs, ROMs, RAMs, magnet or optical cards, or other type of media/machine-readable medium suitable for storing electronic instructions.

Various aspects of the disclosure may be described through the use of flowcharts. Often, a single instance of an aspect of the present disclosure may be shown. As is appreciated by those of ordinary skill in the art, however, the protocols, processes, and procedures described herein may be repeated continuously or as often as necessary to satisfy the needs described herein. Accordingly, the representation of various aspects of the present disclosure through the use of flowcharts should not be used to limit the scope of the present disclosure.

In a preferred embodiment, the steps of the following methods and algorithms are performed by the sensor 12, unless otherwise stated. However, it is contemplated that the following steps of the present invention may be performed by the sensor 12, the monitor 16, or a combination of both.

The accurate detection of consecutive QRS segments is the technical basis for the measurement of the human heart rate. As in many ECG devices, the algorithm employed by the pulse monitoring and warning system 10 uses the temporal location of the QRS segments to calculate the cardiac interbeat interval, which, in turn, is used to calculate the heart rate. Any interference that causes the sensor to miss one or more QRS segments will affect the algorithm's ability to accurately measure the heart rate. In a preferred embodiment, the sensor 12 uses only two electrodes, compared to the standard minimum of three electrodes used in the prior art. Due to this reduction in the number of electrodes, the system must be smarter in order to eliminate the additional noise or interference inherent in a two electrode system. The BPS sensor of the present invention includes both analog circuitry and software functions to minimize interference.

There are two categories of interference—external and internal. Common external interference sources include EMG spikes, AC power coupling, and electrode-skin impedance variations. External interference from AC power coupling can be minimized through the inclusion of a series of low pass and common mode rejection filters in the analog circuitry. Electrode-skin impedance variations distort the desired ECG signal in two ways—baseline wander and amplitude fluctuations. An electronic baseline drift filter in the analog circuitry can significantly reduce the effect of baseline wander, but does not remove amplitude fluctuations. Software functions may be used to minimize the effect of amplitude fluctuations. Finally, the EMG interference is not deterministic and can be within the same temporal and frequency range as the desired cardiac signal. Thus, EMG interference cannot be easily filtered by traditional filters and must be minimized by software functions.

Internal interference sources include circuit switching noise and P/T segment noise. Circuit switching noise is generated by the sensor itself, and through careful circuit design and process management, these can be readily controlled. P/T segment noise results when either the P or T segment is mistakenly identified as a QRS segment.

The QRS detection algorithm employed in the system of the present invention includes several mechanisms for minimizing the impact of amplitude fluctuation, EMG interference and P/T segment interference. In practice, these mechanisms operate in conjunction to provide a higher probability of QRS segment detection. The mechanisms include: a variable QRS detection amplitude threshold algorithm, a variable QRS temporal search window algorithm, a QRS segment slope/width detector algorithm, and a QRS reacquisition procedure, all of which will be discussed in further detail below.

Figure 2:
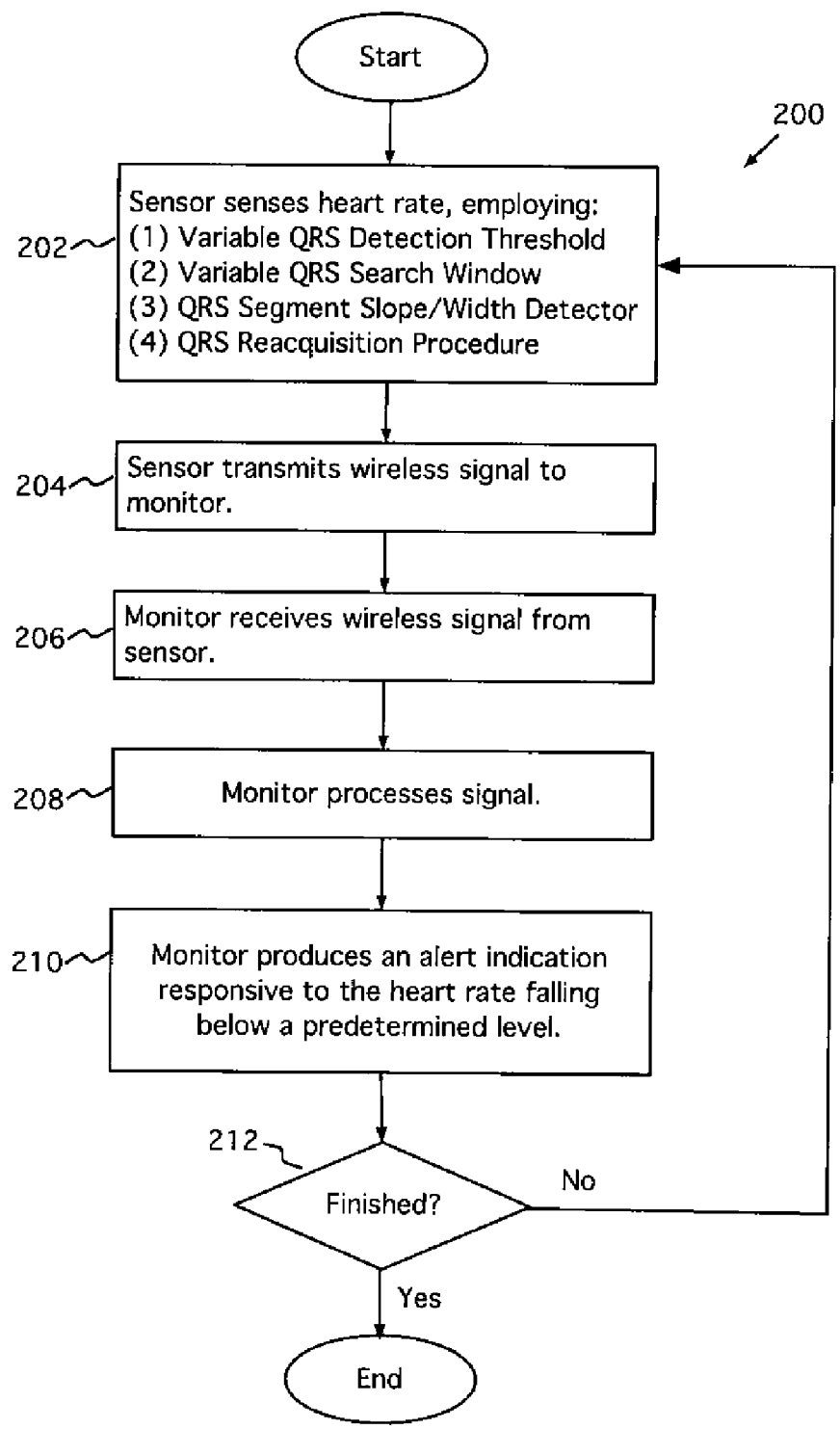
FIG. 2 is a flowchart illustrating an exemplary embodiment of a process for QRS acquisition and tracking in accordance with the present invention.

FIG. 2 is a flowchart illustrating an exemplary embodiment of a process for QRS acquisition and tracking 200 in accordance with the present invention. At step 202, the sensor detects the user's heart rate through the acquisition and tracking of the QRS segment. In doing so, it may employ any of the variable QRS detection threshold algorithm, the variable QRS search window algorithm, the QRS segment slope/width detector algorithm, and the QRS reacquisition procedure, or any combination thereof.

In a preferred embodiment, the present invention uses all three of the variable QRS detection threshold algorithm, the variable QRS search window algorithm, and the QRS segment slope/width detector algorithm. However, it is contemplated that any configuration or combination of the mechanisms may be employed. In another preferred embodiment, the present invention includes the variable QRS detection threshold algorithm at the very least. In yet another preferred embodiment, the present invention uses the variable QRS detection threshold algorithm and at least one of either the variable QRS search window algorithm or the QRS segment slope/width detector algorithm.

At step 204, the sensor then transmits a wireless signal to the monitor. This signal contains information corresponding to the information detected and calculated by the sensor. At step 206, the monitor receives the wireless signal from the sensor, then processes the signal at step 208. At step 210, the monitor produces an alert indication if the heart rate is either too high or too low and falls outside the range of acceptable rates, such as above a predetermined level or below a predetermined level.

Finally, at step 212, it is determined whether or not the process is finished. Situations in which the algorithm may be finished include, but are not limited to, someone turning the system off and the system automatically shutting down or transitioning to a dormant/stand-by mode, where QRS detection is not intended or desired. If the algorithm is finished, the process will come to an end. If the algorithm is not finished, it will repeat at step 202, where the sensor once again senses the heart rate employing any of the QRS detection mechanisms.

As previously mentioned, each QRS detection mechanism will now be discussed in greater detail.

One problem that occurs in the acquisition and tracking of the ECG signal is the occurrence of variations in the amplitude of the ECG waveforms. Many situations can cause the amplitude of the ECG waveform to vary, making it difficult to consistently detect the QRS segment. Failure to compensate for this variability leads to either missed QRS segments or interpretation of noise as a QRS segment. This phenomenon occurs at system start-up and can also occur during normal operation.

At system startup, the analog circuitry will not produce a stable ECG waveform due to the finite initialization period of the interference filters. When the system is activated, the output of the analog circuit will remain at the lower power rail for multiple seconds. As the filters are initialized, the ECG signal begins to increase in amplitude and settle at the midpoint between the upper and lower power rails, optimizing the dynamic range of the system. Similarly, during normal operation, changes in body position can cause changes in the electrode-skin impedance, resulting in amplitude fluctuations in the ECG signal.

Figure 3:
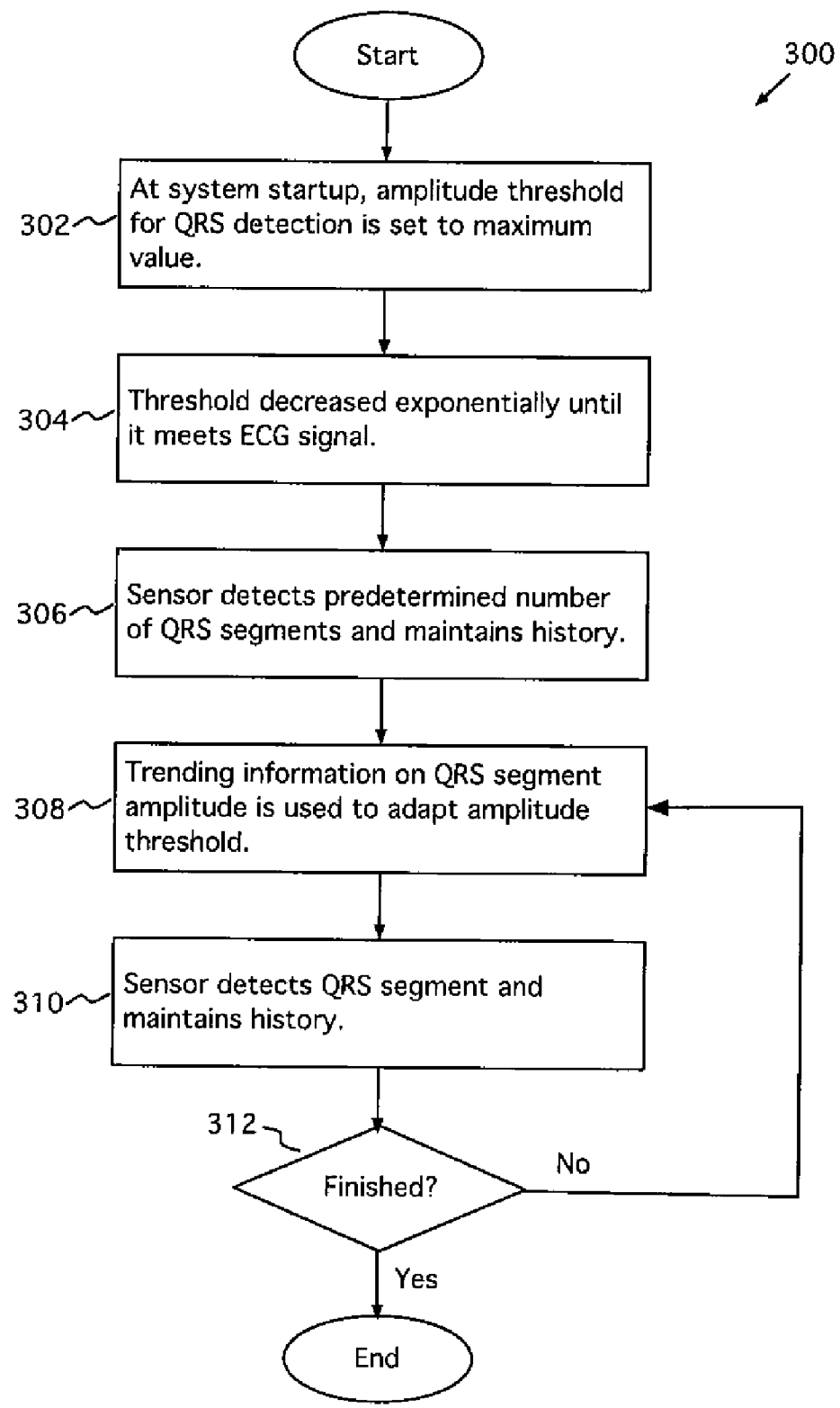
FIG. 3 is a flowchart illustrating an exemplary embodiment of a variable QRS detection amplitude threshold algorithm in accordance with the present invention.

The present invention provides a solution to this problem by employing a variable QRS detection threshold algorithm. The ECG acquisition and tracking algorithm employs a variable QRS detection threshold that is dynamically changed to allow consistent detection of the QRS segment. FIG. 3 is a flowchart illustrating an exemplary embodiment of a variable QRS detection threshold algorithm 300 in accordance with the present invention. At system start-up, the QRS detection threshold is set to the maximum value at step 302, and then decreased exponentially to quickly meet the settling ECG signal at step 304. This concept could best be imagined as two curves (the ECG signal rising and the amplitude threshold falling) changing in their respective directions until they converge and the ECG signal is acquired.

Once the ECG signal has been acquired, the sensor detects a predetermined number of valid QRS segments at step 306, and maintains a history of them, such as by storing their information in memory. The algorithm shifts to tracking mode and uses this history or trending information on the QRS segment amplitude to adapt the threshold at step 308. The amplitudes of previous threshold values and detected QRS segments are used to calculate a new threshold that will be used to detect the next QRS segment. The threshold is increased or decreased to better match the expected changes in the amplitude of the QRS segment. Accordingly, at step 310, the sensor detects the QRS segment using the updated threshold and maintains its history as previously mentioned with respect to step 306. At step 312, it is determined whether or not the algorithm is finished. Situations in which the algorithm may be finished include, but are not limited to, someone turning the system off and the system automatically shutting down or transitioning to a dormant/stand-by mode, where QRS detection is not intended or desired. If the algorithm is finished, the process will come to an end. If the algorithm is not finished, it will repeat at step 308, where the trending information on the QRS segment amplitude will be used to adjust the amplitude threshold.

Another problem that occurs in the acquisition and tracking of the ECG signal is found in trying to isolate the QRS segment in the presence of noise spikes. Noise spikes resulting from EMG and P/T segment interference are commonly present throughout the ECG waveform. These spikes, which can be equal to or greater than the amplitude of the QRS segment, can cause the algorithm to lock onto noise rather than the QRS segment, resulting in the incorrect calculation of the interbeat interval.

The present invention provides a solution to this problem by employing a variable search window algorithm. The acquisition and tracking algorithm employs a variable search window that is used to limit the period of time that the QRS detector is active. Due to the relative stability of a normal heart rate (HR), rapid changes in HR are not expected. This stability allows the sensor to estimate the timing of the next QRS segment and limit the time for detection of the QRS segment to that interval, effectively masking a majority of the noise spikes. Similar to the algorithm used to adjust the QRS threshold, trending information on prior interbeat intervals as well as the expected position of the P and T segments are used to calculate the temporal location and width of the search window.

Figure 4:
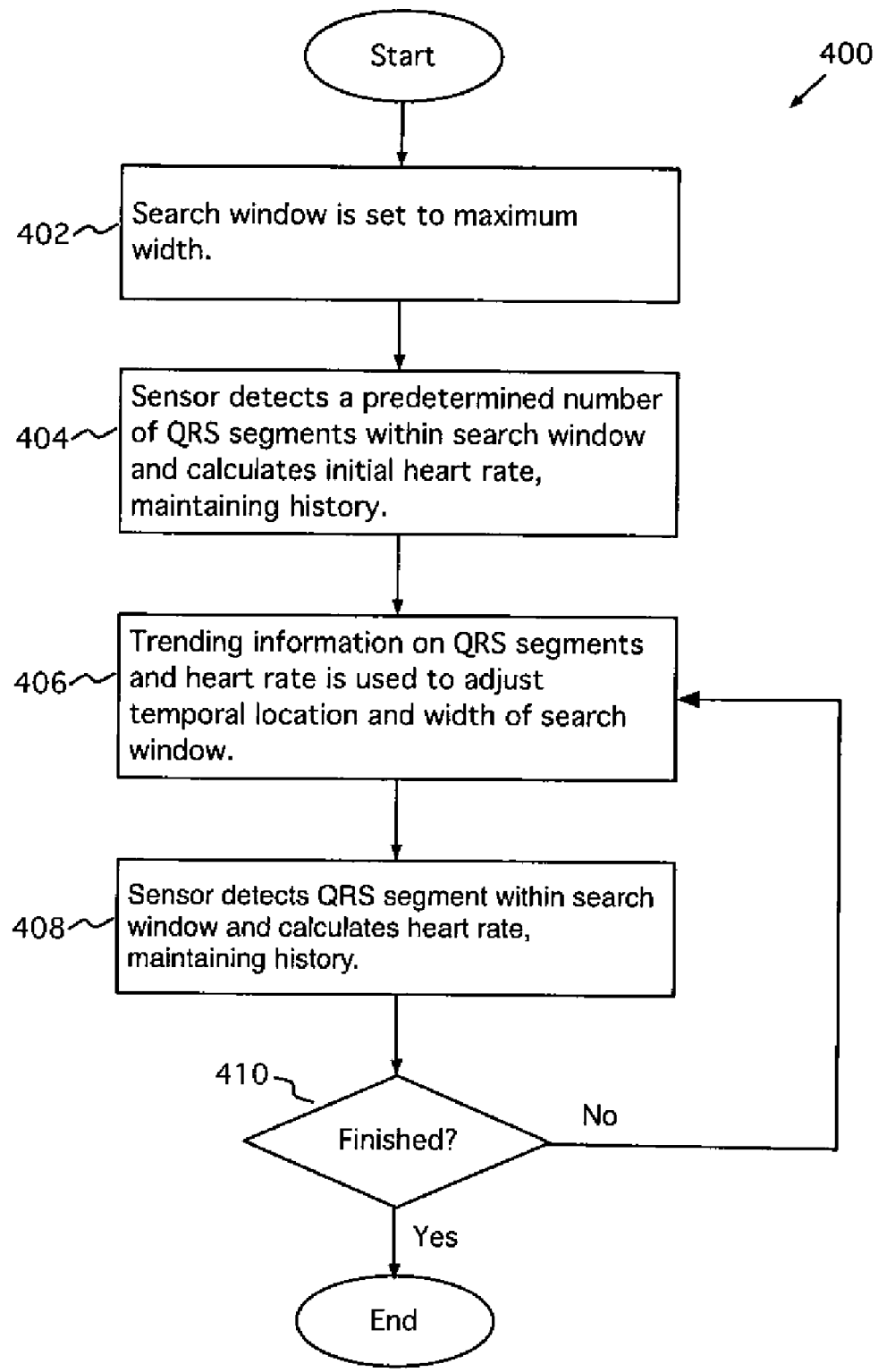
FIG. 4 is a flowchart illustrating an exemplary embodiment of a variable QRS search window algorithm in accordance with the present invention.

FIG. 4 is a flowchart illustrating an exemplary embodiment of a variable QRS search window algorithm 400 in accordance with the present invention. During system start-up and ECG acquisition, the search window is set to the maximum width at step 402, since the actual heart rate is not yet known. The sensor detects a predetermined number of QRS segments and calculates the initial heart rate at step 404, maintaining a history of this information. At step 406, this information on the QRS segments and the heart rate is used to adjust the temporal location and width of the search window. Initially, the search window is reduced, since it begins at a maximum value. The tracking algorithm may then be activated. At step 408, the sensor detects the QRS segment within the updated search window and calculates the heart rate, maintaining the history of this information as previously discussed. At step 410, it is determined whether or not the algorithm is finished, as previously discussed with respect to FIG. 3. If the algorithm is finished, the process will come to an end. If the algorithm is not finished, it will repeat at step 406, where the trending information on the QRS segments and the heart rate will be used to adjust the temporal location and width of the search window.

Yet another problem that occurs in the acquisition and tracking of the ECG signal is in discriminating between valid QRS segments and noise spikes. The variable QRS search window described above dramatically reduces the probability of incorrectly interpreting a noise spike as a QRS segment by limiting the time the QRS detector is active. However, it is still possible that a noise spike can occur during the active time of the QRS detector.

The present invention provides a solution to this problem by employing a QRS segment slope/width detector algorithm to discriminate between valid QRS segments and noise spikes. The shape of the QRS segment is well known and differs from noise waveforms. Noise spikes from EMG sources are typically characterized by fast rising/falling edges and are very short in duration. Conversely, P/T segment noise is characterized by slow edges and is longer in duration. The QRS segment slope/width detector algorithm of the present invention contains a template of the QRS segment and uses this template to discriminate between the QRS segment and noise. The template consists of two key parameters—segment width and segment slope. The segment width parameter is defined as the average QRS segment width and expected variance, while the segment slope parameter is defined as the expected slope of the rising and falling edges of the QRS segment based on the actual width.

Figure 5:
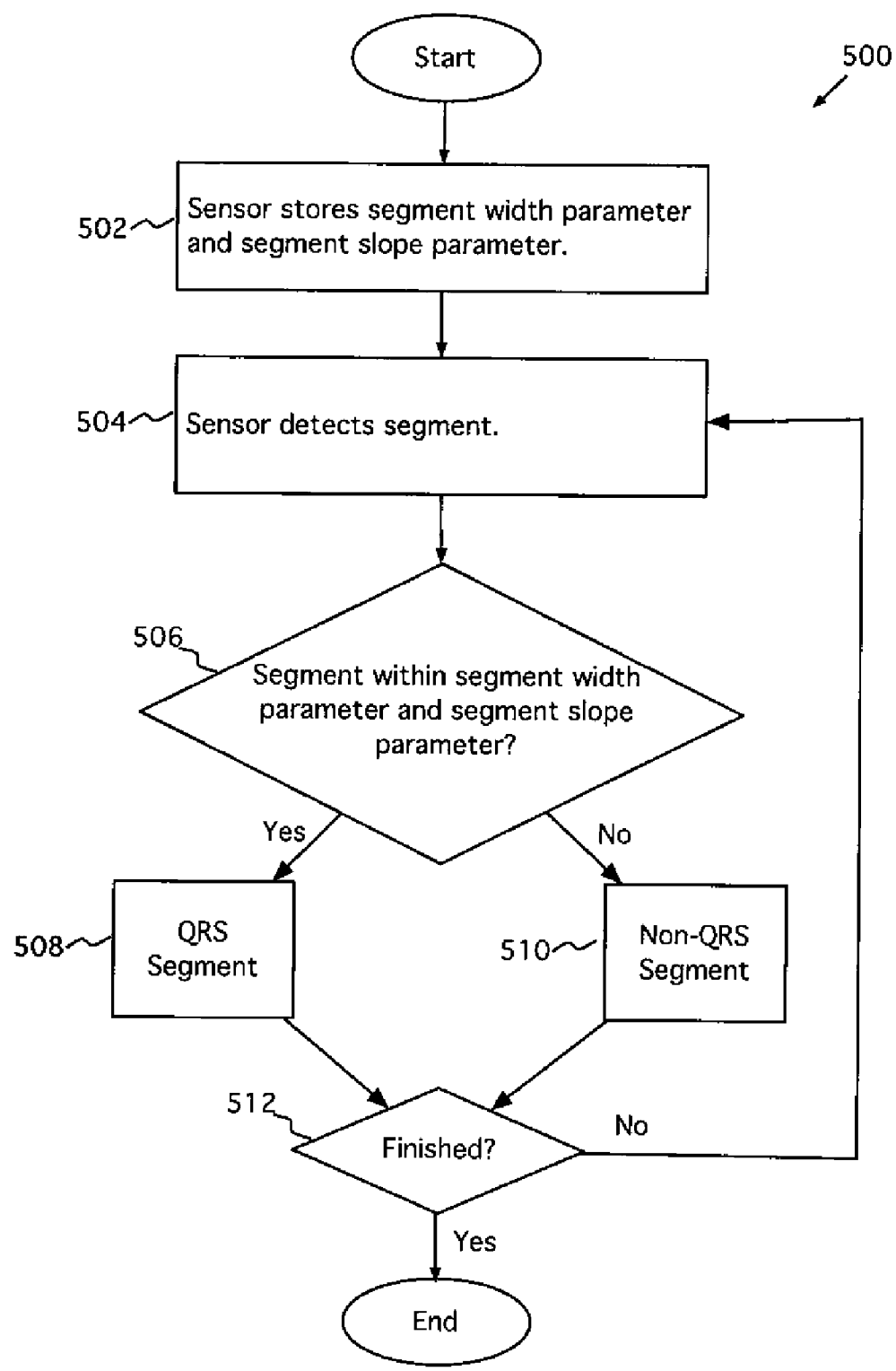
FIG. 5 is a flowchart illustrating an exemplary embodiment of a QRS segment slope/width detector algorithm in accordance with the present invention.

FIG. 5 is a flowchart illustrating an exemplary embodiment of a QRS segment slope/width detector algorithm 500 in accordance with the present invention. At step 502, the sensor stores the segment width parameter and the segment slope parameter in its memory. At step 504, the sensor detects a segment. At step 506, it is determined whether or not the detected segment satisfies both the segment width parameter and the segment slope parameter. If the segment satisfies both parameters, then it is determined to be a valid QRS segment at step 508, and therefore treated as such by the system in its monitoring. The process then proceeds to step 512, where it is determined whether or not the algorithm is finished, as previously discussed. If the algorithm is finished, the process will come to an end. If the algorithm is not finished, it will repeat at step 504, where the sensor detects another segment. If the segment does not satisfy both parameters, then it is determined not to be a valid QRS segment at step 510, and therefore treated as such by the system in its monitoring. The process then proceeds to step 512, where it is determined whether or not the algorithm is finished, as previously discussed.

One other problem that occurs in the acquisition and tracking of the ECG signal is the loss of the ECG signal. Through the application of the three previously discussed QRS detection mechanisms, the system is usually able to acquire and track the ECG signal. However, occasionally, large amounts of noise can cause the system to lose the actual ECG signal and make it unable to track the signal.

The present invention provides a solution to this signal loss problem by employing a QRS reacquisition procedure. The acquisition algorithm includes a QRS reacquisition procedure to re-lock onto the ECG signal. This procedure has two modes of operation to contend with, normal and worst-case scenarios. When the algorithm does not detect a valid QRS segment, it initiates the normal reacquisition mode, gradually decreasing the amplitude threshold and gradually increasing the search window. If this procedure is unsuccessful in reacquiring the signal and the minimum amplitude threshold is reached, the algorithm switches to the original acquisition procedure used during system initialization, such as setting the amplitude threshold to a maximum value and decreasing it exponentially until it meets the ECG signal as previously discussed.

Figure 6:
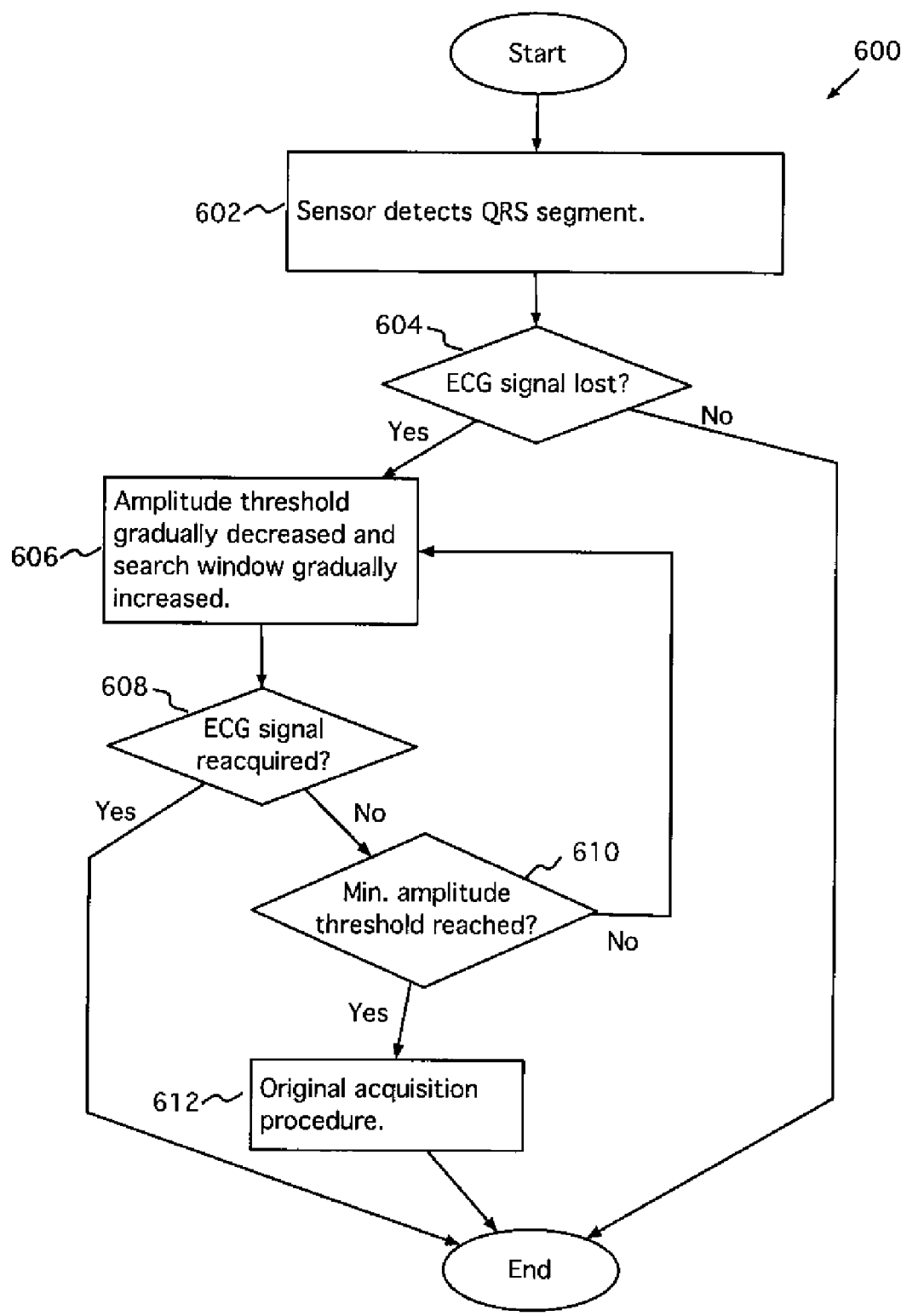
FIG. 6 is a flowchart illustrating an exemplary embodiment of a QRS reacquisition algorithm in accordance with the present invention.

FIG. 6 is a flowchart illustrating an exemplary embodiment of a QRS reacquisition algorithm 600 in accordance with the present invention. At step 602, the sensor detects the QRS segment. At step 604, it is determined whether or not the ECG signal has been lost. If the signal has not been lost, then no reacquisition is required, and the procedure comes to an end. If the signal has been lost (i.e. a valid QRS segment is not detected within the current temporal search window), then the method proceeds to step 606, where the amplitude threshold is gradually decreased and the search window is gradually increased. At step 608, it is determined whether or not the ECG signal has been reacquired. If the signal has been reacquired, the then procedure ends. If the ECG signal has not been reacquired, then it is determined at step 610 whether or not the minimum amplitude threshold has been reached (i.e., whether the amplitude threshold cannot be decreased any more). If the minimum amplitude threshold has not been reached, then the procedure repeats at step 606, where the threshold is decreased and the search window is increased. If the minimum amplitude threshold has been reached, then the method proceeds to step 612, where the original acquisition procedure, such as the one used at start-up in FIG. 3, is used before the procedure comes to an end.

As an alternative to the variable QRS detection threshold discussed above with respect to FIG. 3, a different algorithm that uses an approximation of the standard deviation of the ECG waveform may be used to define the amplitude threshold. As previously discussed, the variable amplitude threshold may be initially set to a maximum value and decreased exponentially until potential QRS segments in the received ECG waveform exceed the threshold. These peaks are then qualified by the QRS temporal search window and QRS segment slope/width detector components to determine if a legitimate QRS segment is present. Once a series of valid QRS segments are detected, the algorithm identifies subsequent QRS segments and, based on the separation between the segments, calculates the heart rate. If at any time, the amplitude threshold is reduced to the minimum level without detection of valid QRS segments, the amplitude threshold and temporal window are reset to their initial values and the acquisition process is repeated.

However, the ECG waveform may have a considerable amount of amplitude variation. This amplitude variation can have two negative effects. It can lead to the occasional failure to detect valid QRS segments and the excessive employment of the reacquisition algorithm. These effects can result in the incorrect calculation of the heart rate or excessive delays in calculating the heart rate.

The present invention includes an alternative variable threshold algorithm that may replace the previous algorithm with a new threshold mechanism that utilizes statistical observations of the received ECG waveform. This new technique is much less sensitive to amplitude variations of the QRS segment, and therefore, is less likely to fail to detect valid QRS segments.

Figure 7:
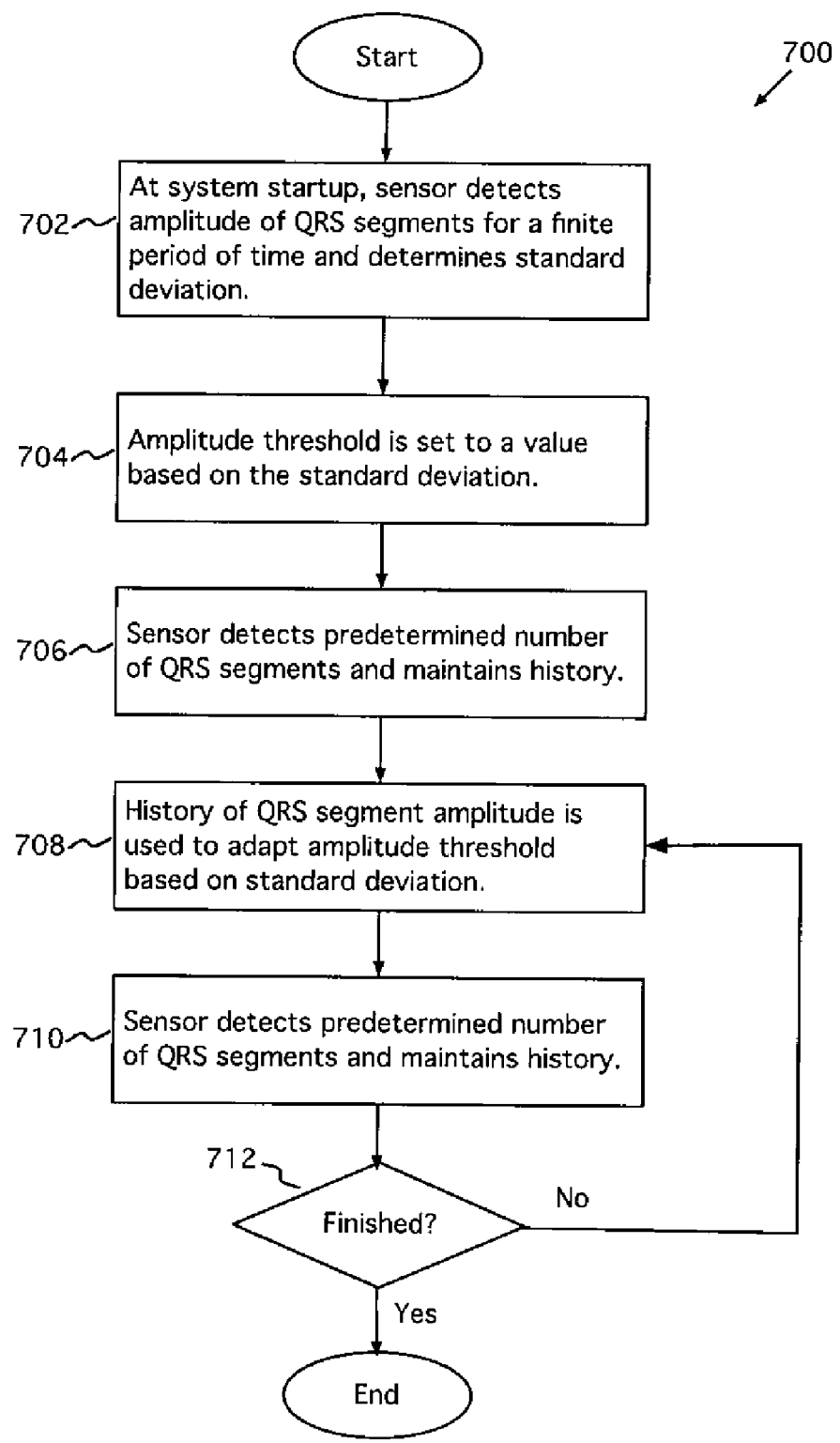
FIG. 7 is a flowchart illustrating an exemplary embodiment of an alternative variable QRS detection amplitude threshold algorithm in accordance with the present invention.

This alternative algorithm uses an approximation of the standard deviation of the ECG waveform to define the amplitude threshold. FIG. 7 is a flowchart illustrating an exemplary embodiment of this alternative variable QRS detection amplitude threshold algorithm 700 in accordance with the present invention.

At system start-up at step 702, the standard deviation is calculated for a finite period of time that is equivalent to a limited number of cardiac cycles based on the minimum detectable heart rate. The actual time period used for the standard deviation is dependent on the desired probability of detection and the processing and memory resources of the device.

At step 704, the amplitude threshold is then set to a value based on the standard deviation. In a preferred embodiment, the amplitude threshold is set to a value approximately twice the value of the standard deviation, effectively eliminating a majority of the noise, while allowing for the detection of potential QRS segments of varying amplitudes.

At step 706, the sensor detects a predetermined number of valid QRS segments using the amplitude threshold and maintains a history of them, including information about the amplitude. All potential QRS segments that exceed the threshold may then be qualified with the previously discussed techniques, such as temporal windowing or slope width detection, in order to isolate the valid QRS segments.

At step 708, the algorithm uses this history of the QRS segment amplitude to adapt the threshold based on the standard deviation. Previously detected and maintained amplitudes may be used to calculate a new threshold that will be used to detect the next QRS segment. For example, a predetermined number of the most recent amplitude measurements may be used to calculate the standard deviation and adapt the amplitude threshold. The value of the standard deviation can be recalculated on a regular basis or any time the system is unable to track and acquire the QRS segments in the received waveform.

In a preferred embodiment, an approximation of the standard deviation ($SD_a$) and the resulting amplitude threshold can be calculated as follows:

$$SD_a = \frac{1}{N}\left[\sum_{i=1}^{N}(x_i^2 - x_a^2)\right]^{1/2} \text{; where}$$

N=number of samples used in the calculation
$x_i$=individual samples from the ECG waveform
$x_a$=arithmetic average of the samples over the period defined by N The amplitude threshold ($A_{QRS}$) then becomes:

$A_{QRS}=2(SD_a)$

While the amplitude threshold is preferably set and maintained at a value of approximately twice the value of the standard deviation, it is contemplated that the use of other multiples of the standard deviation are within the scope of the present invention as well.

At step 710, the sensor detects the QRS segment using the updated threshold and maintains its history as previously mentioned with respect to step 706. At step 712, it is determined whether or not the algorithm is finished. Situations in which the algorithm may be finished include, but are not limited to, someone turning the system off and the system automatically shutting down or transitioning to a dormant/stand-by mode, where QRS detection is not intended or desired. If the algorithm is finished, the process will come to an end. If the algorithm is not finished, it will repeat at step 708, where the history on the QRS segment amplitude will be used to adjust the amplitude threshold based on the calculation of the standard deviation.

The use of ECG technology to detect and measure heart rate is well accepted by the medical community but does have some serious limitations. Most notably, the ECG waveform is susceptible to interference from both external and internal noise sources. The unique combination of the QRS detection mechanisms of the present invention operating in conjunction provides a robust system that can acquire and track the human ECG signal in the presence of noise.

Although described herein to monitor the heart rate of infants, the disclosed pulse monitoring and warning system could also be utilized with the elderly or people of any age.

While embodiments and applications of this invention have been shown and described, it would be apparent to those skilled in the art that many more modifications than mentioned above are possible without departing from the inventive concepts herein.

What is claimed is:

1. A system for monitoring a person's heart rate comprising:
    a sensor disposable over said person's heart and configured to detect QRS segments from an electrocardiogram (ECG) signal corresponding to said person's heart rate using an amplitude threshold and a search window, wherein said sensor is configured to automatically adjust said amplitude threshold based on previous QRS segment measurements and transmit a wireless signal to a monitor, said wireless signal comprising information about said detected QRS segments and corresponding heart rate;

said sensor further configured to automatically adjust the temporal location and width of said search window by:
set the width of said search window to a maximum value;
detect a predetermined number of QRS segments using said search window;
store information about said detected predetermined number of QRS segments in memory;
automatically adjust the width of said search window based on said stored information; and
detect subsequent QRS segments using said adjusted search window;
said monitor configured to receive said wireless signal from said sensor, process said signal from said sensor, and produce an alert indication responsive to said person's heart rate falling below a predetermined level based on said information in said wireless signal.

2. A system for monitoring a person's heart rate comprising:
a sensor disposable over said person's heart and configured to detect QRS segments from an electrocardiogram (ECG) signal corresponding to said person's heart rate using an amplitude threshold and a search window, wherein said sensor is configured to automatically adjust said amplitude threshold based on previous QRS segment measurements and transmit a wireless signal to a monitor, said wireless signal comprising information about said detected QRS segments and corresponding heart rate;
said sensor configured to:
set said amplitude threshold to a maximum value;
decrease said amplitude threshold from said maximum value until said sensor detects a QRS segment;
detect a predetermined number of QRS segments using said amplitude threshold;
store information about said detected predetermined number of QRS segments in memory;
automatically adjust said amplitude threshold based on said stored information; and
detect subsequent QRS segments using said adjusted amplitude threshold;
said monitor configured to receive said wireless signal from said sensor, process said signal from said sensor, and produce an alert indication responsive to said person's heart rate falling below a predetermined level based on said information in said wireless signal.

3. A method for monitoring a person's heart rate using a sensor and a monitor, said sensor disposable over said person's heart, said method comprising the steps of:
said sensor detecting QRS segments from an electrocardiogram (ECG) signal corresponding to said person's heart rate using an amplitude threshold and a search window, wherein said amplitude threshold is automatically adjusted based on previous QRS segment measurements;
said sensor automatically adjusting the temporal location and width of said search window based on said previous QRS segment measurements by:
said sensor setting the width of said search window to a maximum value;
said sensor detecting a predetermined number of QRS segments using said search window;
said sensor storing information about said detected predetermined number of QRS segments in memory; and
said sensor automatically adjusting the width of said search window based on said stored information; and
said sensor detecting subsequent QRS segments using said adjusted search window;
said sensor transmitting a wireless signal to said monitor, said wireless signal comprising information about said detected subsequent QRS segments and corresponding heart rate;
said monitor receiving said wireless signal from said sensor;
said monitor processing said signal from said sensor; and
said monitor producing an alert indication responsive to said person's heart rate falling below a predetermined level based on said information in said wireless signal.

4. A method for monitoring a person's heart rate using a sensor and a monitor, said sensor disposable over said person's heart, said method comprising the steps of:
said sensor detecting QRS segments from an electrocardiogram (ECG) signal corresponding to said person's heart rate using an amplitude threshold and a search window, wherein said amplitude threshold is automatically adjusted based on previous QRS segment measurements by:
said sensor setting said amplitude threshold to a maximum value;
said sensor decreasing said amplitude threshold from said maximum value until said sensor detects a QRS segment;
said sensor detecting a predetermined number of QRS segments using said amplitude threshold;
said sensor storing information about said detected predetermined number of QRS segments in memory;
said sensor automatically adjusting said amplitude threshold based on said stored information; and
said sensor detecting subsequent QRS segments using said adjusted amplitude threshold;
said sensor transmitting a wireless signal to said monitor, said wireless signal comprising information about said detected subsequent QRS segments and corresponding heart rate;
said monitor receiving said wireless signal from said sensor;
said monitor processing said signal from said sensor; and
said monitor producing an alert indication responsive to said person's heart rate falling below a predetermined level based on said information in said wireless signal.

5. A method for monitoring a person's heart rate using a sensor and a monitor, said sensor disposable over said person's heart, said method comprising the steps of:
said sensor detecting QRS segments from an electrocardiogram (ECG) signal corresponding to said person's heart rate using an amplitude threshold and a search window, by;
detecting a predetermined number of QRS segments using said amplitude threshold;
storing information about said detected predetermined number of QRS segments in memory;
calculating a standard deviation of the amplitude for said detected predetermined number of QRS segments;
automatically adjusting said amplitude threshold based on said standard deviation; and
detecting subsequent QRS segments using said adjusted amplitude threshold;
said sensor transmitting a wireless signal to said monitor, said wireless signal comprising information about said detected subsequent QRS segments and corresponding heart rate;

said monitor receiving said wireless signal from said sensor;

said monitor processing said signal from said sensor; and said monitor producing an alert indication responsive to said person's heart rate falling below a predetermined level based on said information in said wireless signal.

6. The method of claim 5, wherein said step of automatically adjusting said amplitude threshold comprises automatically setting said amplitude threshold to a value that is approximately twice the value of said standard deviation.

7. The method of claim 5, wherein said step of detecting said subsequent QRS segments further comprises said sensor using a template of QRS segment width and QRS segment slope to discriminate between each of said subsequent QRS segments and noise.

8. The method of claim 5, wherein said automatically adjusting said amplitude threshold is performed after losing said ECG signal.

9. The method of claim 8, further comprising gradually decreasing said amplitude threshold and gradually increasing the width of said search window until said ECG signal is reacquired.

10. The method of claim 5, wherein said monitor is equipped with a speaker for providing said alert indication.

11. The method of claim 5, wherein only one said sensor is used to transmit said signal to said monitor.

12. The method of claim 11, wherein said only one said sensor comprises only two electrodes.

13. A system for monitoring a person's heart rate comprising:

a sensor disposable over said person's heart and configured to detect QRS segments from an electrocardiogram (ECG) signal corresponding to said person's heart rate using an amplitude threshold and a search window, wherein said sensor is configured to automatically adjust said amplitude threshold based on previous QRS segment measurements and transmit a wireless signal to a monitor, said wireless signal comprising information about said detected QRS segments and corresponding heart rate;

said sensor further configured to:

detect a predetermined number of QRS segments using said amplitude threshold, store information about said detected predetermined number of QRS segments in memory, calculate a standard deviation of the amplitude for said detected predetermined number of QRS segments, automatically adjust said amplitude threshold based on said standard deviation, and detect subsequent QRS segments using said adjusted amplitude threshold;

said monitor configured to receive said wireless signal from said sensor, process said signal from said sensor, and produce an alert indication responsive to said person's heart rate falling below a predetermined level based on said information in said wireless signal.

14. The system of claim 13, wherein said monitor is equipped with a speaker for providing said alert indication.

15. The system of claim 13, wherein said sensor is further configured to automatically set said amplitude threshold to a value that is approximately twice the value of said standard deviation.

16. The system of claim 13, wherein said sensor is further configured to automatically adjust said amplitude threshold after losing said ECG signal.

17. The system of claim 16, wherein said sensor is further configured to gradually decrease said amplitude threshold and gradually increase the width of said search window until said ECG signal is reacquired.

18. The system of claim 13, wherein said sensor comprises only two electrodes.

19. The system of claim 13, wherein said sensor is further configured to use a template of QRS segment width and QRS segment slope to discriminate between each of the subsequent QRS segments and noise.

* * * * *